US012257219B2

(12) United States Patent
Muthaiyyan et al.

(10) Patent No.: US 12,257,219 B2
(45) Date of Patent: *Mar. 25, 2025

(54) STORAGE STABLE AQUEOUS PARENTERAL SOLUTIONS COMPRISING DICLOFENAC

(71) Applicant: RK PHARMA INC., Pearl River, NJ (US)

(72) Inventors: Kannan Essakimuthu Muthaiyyan, Gujarat (IN); Debjani Manoj Singh, Gujarat (IN); Nirav Ishwarlal Khatri, Gujarat (IN); Sushrut Krishnaji Kulkarni, Maharashtra (IN); Alex Kochukunju George, Gujarat (IN); Sushilkumar Dhanaji Patil, Kolhapur (IN); Jay Shantilal Kothari, Pennington, NJ (US)

(73) Assignee: RK PHARMA INC., Pearl River, NY (US)

( * ) Notice: Subject to any disclaimer, the term of this patent is extended or adjusted under 35 U.S.C. 154(b) by 193 days.

This patent is subject to a terminal disclaimer.

(21) Appl. No.: 18/328,397

(22) Filed: Jun. 2, 2023

(65) Prior Publication Data

US 2023/0301952 A1    Sep. 28, 2023

Related U.S. Application Data

(63) Continuation of application No. 17/032,395, filed on Sep. 25, 2020, now Pat. No. 11,707,443.

(30) Foreign Application Priority Data

Sep. 26, 2019 (IN) .............................. 201921038953

(51) Int. Cl.
| | | |
|---|---|---|
| *A61K 31/196* | (2006.01) | |
| *A61K 9/00* | (2006.01) | |
| *A61K 47/02* | (2006.01) | |
| *A61K 47/26* | (2006.01) | |
| *A61K 47/32* | (2006.01) | |
| *A61M 5/20* | (2006.01) | |

(52) U.S. Cl.
CPC .......... *A61K 31/196* (2013.01); *A61K 9/0019* (2013.01); *A61K 47/02* (2013.01); *A61K 47/26* (2013.01); *A61K 47/32* (2013.01); *A61M 5/20* (2013.01)

(58) Field of Classification Search
CPC .... A61K 31/196; A61K 47/32; A61K 9/0019; A61K 45/06; A61K 9/08; A61K 47/02; A61K 47/26; A61M 5/20
See application file for complete search history.

(56) References Cited

U.S. PATENT DOCUMENTS

| | | |
|---|---|---|
| 4,711,906 A | 12/1987 | von Stetten |
| 5,024,998 A | 6/1991 | Bodor |
| 5,389,681 A | 2/1995 | Galli |
| 5,679,660 A | 10/1997 | Bodley et al. |
| 5,929,115 A | 7/1999 | Takeuchi et al. |
| 8,580,954 B2 | 11/2013 | Wright et al. |
| 8,946,292 B2 | 2/2015 | Wright et al. |
| 9,211,251 B2 | 12/2015 | Patel et al. |
| 9,427,446 B2 | 8/2016 | Irianni et al. |
| 11,110,073 B2 | 9/2021 | Patil et al. |
| 2005/0282776 A1 | 12/2005 | Zoppetti et al. |
| 2012/0142779 A1 | 6/2012 | Penkler et al. |
| 2015/0105467 A1 | 4/2015 | Wright et al. |
| 2016/0038414 A1 | 2/2016 | Okumu et al. |
| 2018/0271815 A1 | 9/2018 | Patil et al. |
| 2021/0369659 A1 | 12/2021 | Patil et al. |

FOREIGN PATENT DOCUMENTS

| | | |
|---|---|---|
| CN | 106214632 A | 12/2016 |
| IN | 1382/MUM/2008 | 12/2009 |
| IN | 1438/MUM/2012 | 1/2013 |
| WO | 2005092387 A1 | 10/2005 |
| WO | 2014102824 A1 | 7/2014 |
| WO | 2016170401 A1 | 10/2016 |
| WO | 2016205172 A1 | 12/2016 |

OTHER PUBLICATIONS

Yu-Chang et al., Journal of parenteral drug association, 1980, 34, 452-462.
Stephanie et al., PDA J. Pharm Sci. and Tech., 1996, 50, 330-342.
Padiyar et al., International Journal of Advanced Pharmaceutics, 2016, 6 (2), 78-84.
Enam Khalil et al., Drug Development and Industrial Pharmacy, 2000, 26 (4), 375-381.

*Primary Examiner* — Savitha M Rao
(74) *Attorney, Agent, or Firm* — Ladas & Parry LLP

(57) ABSTRACT

The present invention relates to stable, aqueous, parenteral solutions comprising diclofenac and polyvinylpyrrolidone, wherein the solutions are for parenteral (subcutaneous, intravenous and/or intramuscular) administration to a mammal.

9 Claims, No Drawings

STORAGE STABLE AQUEOUS PARENTERAL SOLUTIONS COMPRISING DICLOFENAC

RELATED APPLICATION

This application is a continuation application and claims priority to and the benefit of U.S. patent application Ser. No. 17/032,395 dated 25 Sep. 2020 which claims priority from IN 201921038953 filed 26 Sep. 2019 and the contents of which are incorporated herein in its entirety.

FIELD OF THE INVENTION

The present invention relates to stable, aqueous, parenteral solutions comprising diclofenac and polyvinylpyrrolidone, wherein the solutions are for parenteral (subcutaneous, intravenous and/or intramuscular) administration. The invention relates to the pharmacokinetic profile of diclofenac formulation administered via the parenteral route to human subjects. The invention also relates to method of treatment of migraine and/or pain and a kit containing pre-filled syringe of the parenteral solution. It also relates to processes for preparing such solutions.

BACKGROUND OF THE INVENTION

Diclofenac is widely prescribed analgesic and anti-inflammatory agent and may be administered via oral as well as parenteral route. Oral dose of diclofenac ranges from 100 mg to 200 mg per day, while parenteral dose ranges from 75 to 150 mg per day.

U.S. Pat. No. 5,389,681 discloses sterilizable parenteral solution comprising a diclofenac salt, solubilisers such as 1,2-propylene glycol or polyethylene glycol 300-400, stabilisers such as glutathione or N-acetyl cysteine and a carrier liquid, such as water.

Indian Application No. 1382/MUM/2008 discloses injectable composition comprising diclofenac, polyoxyl 35 castor oil, benzyl alcohol, sodium sulphite, disodium EDTA and water as a principal solvent.

U.S. Publication No. 2012/0142779 discloses parenteral aqueous solution comprising either (a) diclofenac or a pharmaceutically acceptable diclofenac salt and a cyclodextrin, or (b) an inclusion complex of diclofenac or a pharmaceutically acceptable diclofenac salt and a cyclodextrin, or a mixture of both.

Indian Application No. 1438/MUM/2012 discloses injectable composition comprising diclofenac and/or its acceptable salts, macrogol 15 hydroxystearate and pharmaceutically acceptable excipients.

Padiyar A. et al., International Journal of Advanced Pharmaceutics, 2016, 6 (2), 78-84, discloses a mixed solvency concept using solid solublizers for preparing injectable composition comprising diclofenac sodium in concentration 75 mg with a low volume of injection to 1 mL.

International Publication No. (PCT) WO 2016/170401 discloses injectable composition comprising diclofenac or water soluble salts thereof, in a solvent system containing water and two or more solubilizers, and optionally, one or more antioxidant (s) and/or one or more buffering agent (s) for administration via intradeltoid along with intragluteal, subcutaneous and slow intravenous route.

Migraine is a chronic neurovascular disorder characterized by recurrent attacks of often severe headache, typically accompanied by nausea/vomiting and sensitivity to light and/or sound. Pharmacologic approaches to the treatment of migraine include drugs to treat acute migraine attacks as they arise (acute treatment of migraine), and drugs to reduce the frequency of migraine attacks (preventive treatment).

CAMBIA® (Diclofenac Potassium for Oral Solution) is an oral formulation approved by the USFDA for the acute treatment of migraine attacks with or without aura in adults 18 years of age or older.

During acute migraine, gastrointestinal motility is reduced which results in impaired drug absorption. Also, nausea or vomiting accompanied with migraine, causes difficulty to the patient for oral medication. First pass metabolism of diclofenac potassium after oral administration of CAMBIA® has resulted in only approximately 50% bioavailability of the drug. There still exists a need for a storage stable solution which enables safe and efficacious administration of concentrated solution of diclofenac either without pain or with minimal pain at the site of administration, and also suitable for administration via subcutaneous injection route to offer the advantages over existing oral dosage form, viz., providing quick onset of action, providing better/improved safety and pharmacokinetic profile and/or providing better/improved patient convenience. A subcutaneous administration of a drug, as an alternate route, for the treatment of migraine can be a better option to avoid the above mentioned drawbacks.

SUMMARY OF THE INVENTION

In one general aspect, the present invention provides a stable, aqueous, parenteral solution comprising diclofenac and polyvinylpyrrolidone (PVP).

In another general aspect, the present invention provides a process for preparing the parenteral solution comprising diclofenac and polyvinylpyrrolidone.

In another general aspect, the present invention provides a method for the treatment of pain and inflammation, the method comprising administering to a human being in need thereof, a parenteral solution of the present invention either without pain or with minimal pain at the site of administration when administered via intravenous route or subcutaneous injection route.

In another general aspect, the present invention provides a kit comprising an autoinjector which contains a pre-filled syringe (a pre-filled syringe assembled/placed in an autoinjector), wherein the pre-filled syringe (PFS) is filled with a solution of a therapeutically effective amount of diclofenac sodium. The autoinjector provides convenience to the patient for self-administration.

In another general aspect, the present invention provides a method for the treatment of the acute treatment of migraine attacks with or without aura in adults (18 years of age or older), the method comprising administering a solution comprising diclofenac via subcutaneous route.

In another general aspect, the present invention provides pharmacokinetic profile of diclofenac composition by subcutaneous and intravenous route performed in humans.

In another general aspect, the present invention provides a comparative pharmacokinetic profile of diclofenac oral composition and subcutaneous composition performed in humans.

In another general aspect, the present invention provides an open label, randomized, four period, four-treatment, four-sequence, crossover, balanced, single dose comparative bioavailability study of diclofenac composition performed in humans.

In another general aspect, the present invention provides pharmacokinetic profile of diclofenac composition by subcutaneous and intravenous route performed in humans.

The details of one or more embodiments of the invention are set forth in the description below. Other features, objects and advantages of the invention will be apparent from the description.

DETAILED DESCRIPTION OF THE INVENTION

The present invention provides a stable, aqueous, parenteral solution comprising diclofenac and one or more pharmaceutically acceptable excipients.

The aqueous parenteral solution is in the form of a clear solution comprising diclofenac and polyvinylpyrrolidone.

The term "diclofenac" as used herein, unless and otherwise specifically mentioned, encompasses diclofenac base as well as its pharmaceutically acceptable salts, for example, diclofenac sodium and diclofenac potassium.

The terms "pharmaceutically acceptable salt" or "salt" includes, but is not limited to: (1) acid addition salts, formed by reacting the freebase form of a therapeutic agent with a pharmaceutically acceptable: inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like; (2) salts formed when an acidic proton present in the parent therapeutic agent is replaced by a metal ion, e.g., an alkali metal ion (e.g. lithium, sodium, potassium), an alkaline earth ion (e.g. magnesium, or calcium), or an aluminum ion. In some cases, therapeutic agents may coordinate with an organic base, such as, but not limited to, ethanolamine, diethanolamine, triethanolamine, tromethamine, N-methylglucamine, dicyclohexylamine, tris(hydroxymethyl)methylamine. In other cases, therapeutic agents form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

The storage stable aqueous parenteral solution may be administered via parenteral route, for example, intramuscular (intradeltoid, intragluteal etc.), subcutaneous, intravenous infusion or intravenous bolus route.

The term "about" as used herein, refers to encompass +/−20%, 15%, 10%, 5%, 2%, 1%, 0.5%, or 0.25% of the numerical value of the number with which it is being used.

The term "between" as used herein for the purpose of defining ranges, is inclusive of the lower and upper number of the range.

The term "storage stable" as used herein, refers to any composition comprising a drug having sufficient physical and chemical stability to allow storage at a convenient temperature, such as between about 0° C. and about 40° C., for a commercially reasonable period of time. The term "physical stability" refers to maintenance of color or colorless state, dissolved oxygen level, head space oxygen level, and particulate matter size. The term "chemical stability" relates to formation of drug-related impurities in terms of total impurities, known impurities and single maximum unknown impurity, up to allowed limits by the Regulatory Agency. For pharmaceutical products, stability is required for commercially relevant time after manufacturing, such as for about 1, 3, 6, 12, 18, 24 or 36 months, during which a product is kept in its original packaging under specified storage conditions. The term composition includes the solution prepared in accordance with the present invention.

The term "stable" as used herein, refers to any composition comprising a drug having sufficient physical and chemical stability at the time of manufacturing of the composition.

The term "controlled room temperature" as used herein, refers to the temperature between 20° C. and 25° C.

The term "bioavailability" refers to the percentage of the weight of a therapeutic agent that is delivered into the general circulation of the animal or human being studied. The total exposure (AUC(0-∞)) of a drug when administered intravenously is usually defined as 100% bioavailable.

The term "$T_{max}$" as used herein, unless and otherwise specifically mentioned, means time to achieve maximum concentration of the drug in plasma, achieved after administration of the product (unit for example: minutes/hours).

The term "$C_{max}$" as used herein, unless and otherwise specifically mentioned, means maximum concentration of drug in plasma, achieved after administration of the product (unit for example: ng/mL).

The term "AUC" as used herein, unless and otherwise specifically mentioned, means area under the curve for a plot of concentration of drug in plasma vs. time (unit for example: ng*h/mL).

The term "blood plasma concentration", "blood concentration", "plasma concentration" or "serum concentration" refers to the concentration of a therapeuticagent in the plasma or serum component of blood of a subject.

In one embodiment, the present invention provides a stable parenteral solution comprising diclofenac, polyvinylpyrrolidone and water.

In another embodiment, the present invention provides a stable solution comprising diclofenac, polyvinylpyrrolidone, polysorbate 80, sodium chloride, one or more pH adjusting agents, and water for parenteral administration.

The stable aqueous parenteral solution may comprise diclofenac sodium in a concentration of between about 10 mg/mL and about 500 mg/mL, for example, about 20 mg/mL, about 25 mg/mL, about 30 mg/mL, about 37.5 mg/mL, about 40 mg/mL, about 50 mg/mL, about 60 mg/mL, about 70 mg/mL, about 75 mg/mL, about 80 mg/mL, about 90 mg/mL, about 100 mg/mL, about 125 mg/mL, about 150 mg/mL, about 175 mg/mL, about 200 mg/mL, about 250 mg/mL, about 275 mg/mL, about 300 mg/mL, about 325 mg/mL, about 350 mg/mL, about 375 mg/mL, about 400 mg/mL, about 425 mg/mL, about 450 mg/mL, about 475 mg/mL or about 500 mg/mL.

The stable aqueous parenteral solution may comprise polyvinylpyrrolidone in a concentration of between about 50 mg/mL and about 300 mg/mL, for example, about 60 mg/mL, about 70 mg/mL, about 80 mg/mL, about 100 mg/mL, about 120 mg/mL, about 140 mg/mL, about 160 mg/mL, about 180 mg/mL, about 200 mg/mL, about 220 mg/mL, about 250 mg/mL or about 280 mg/mL.

In another embodiment, the stable aqueous parenteral solution may comprise diclofenac in a concentration of 25 mg/mL, 37.5 mg/mL or 75 mg/mL, wherein upon dilution of the solution with appropriate amount of the D5NS (solution of 5 percent dextrose in saline (0.9% sodium chloride)) or saline solution (0.9% sodium chloride), it may provide a diluted solution for parenteral administration having diclofenac concentration of 0.75 mg/mL, 0.30 mg/mL or 0.15 mg/mL, which remains clear (free of any crystals/precipitates) after storage for 24 hours at controlled room temperature or at 2-8° C.

In one embodiment, the present invention provides a storage stable aqueous parenteral solution comprising diclofenac and one or more pharmaceutically acceptable excipients, wherein the solution retains at least 95% of the diclofenac.

In another embodiment, the present invention provides a storage stable aqueous parenteral solution comprising diclofenac, polyvinylpyrrolidone, polysorbate 80 and water, wherein the solution is storage stable after storage for 12 months at controlled room temperature.

The storage stable aqueous parenteral solution may retain at least 95% of the diclofenac sodium (% assay) after storage for at least 1 month, for example, 2 months, 3 months, 6 months, 12 months, 18 months or 24 months at controlled room temperature (CRT).

The storage stable aqueous parenteral solution may retain at least 95% of the diclofenac sodium (% assay) after storage for at least 1 month, for example, 2 months, 3 months, 6 months, 12 months, 18 months or 24 months at 25° C. temperature and 60% relative humidity (% RH).

The storage stable aqueous parenteral solution may retain at least 95% of the diclofenac sodium (% assay) after storage for at least 1 month, for example, 2 months, 3 months, 6 months, 12 months, 18 months or 24 months at 40° C. temperature and 75% RH.

In another embodiment, the stable aqueous parenteral solution comprising diclofenac is clear (free of any crystals/precipitates) by visual inspection after storage for at least 1 month, for example, 2 months, 3 months, 6 months, 12 months, 18 months or 24 months, at controlled room temperature. The solution may provide the value of absorbance not more than 1, for example, not more then 0.75, 0.5, 0.4, 0.3, 0.2, 0.1 or 0.05. The solution may provide the value of % transmittance not less than 90%, for example, not less than 95%, 96%, 97%, 98%, 99%, 99.5% or 99.9%. The parenteral solution comprising diclofenac of the present invention does not form any precipitate and remains physically stable after storage for more than 2 months, for example, for 3 months, for 6 months, for 12 months, for 18 months, for 24 months or for 36 months when stored at 2° C.-8° C. temperature or at 25±2° C. temperature and 60±5% RH.

In another embodiment, the stable aqueous parenteral solution comprising diclofenac does not contain impurity A (1-(2,6-dichlorophenyl) indolin-2-one) more than 0.5%, for example, 0.4%, 0.3%, 0.2%, 0.1% or 0.05%, by weight of diclofenac, as measured by HPLC after storage for at least 1 month, for example, 2 months, 3 months, 6 months, 12 months, 18 months or 24 months, at controlled room temperature.

In another embodiment, the stable aqueous parenteral solution comprising diclofenac may have a viscosity value of between about 1.5 cP and 7.5 cP, for example, 2 cP, 2.5 cP, 3 cP, 3.5 cP, 4 cP, 4.5 cP, 5 cP, 5.5 cP, 6 cP, 6.5 cP or 7 cP.

In another embodiment, the stable aqueous parenteral solution comprising diclofenac may have an osmolality value of between about 200 mOsm and about 600 mOsm, for example, about 250 mOsm, about 300 mOsm, about 350 mOsm, about 400 mOsm, about 450 mOsm, about 500 mOsm or about 550 mOsm.

In another embodiment, the stable aqueous parenteral solution comprising diclofenac may have a pH of between about 7 and about 10, for example, about 7.5, about 8, about 8.5, about 9 or about 9.5.

The suitable pharmaceutically acceptable excipients for the solution of the present invention may include one or more pharmaceutically acceptable solvents, solubilizers, stabilizers, preservatives, antioxidants, surfactants, buffering agents, nucleation inhibitors, pH adjusting agents and isotonicity adjusting agents.

Examples of suitable pharmaceutically acceptable solvents may include, but not limited to, water for injection, and the like.

Examples of suitable pharmaceutically acceptable solubilizers may include, but not limited to benzyl benzoate, castor oil, cottonseed oil, N, N dimethylacetamide, dehydrated ethanol, glycerol, N-methyl-2-pyrrolidone, diethanolamine, L-arginine, peanut oil, poppyseed oil, safflower oil, sesame oil, soybean oil, vegetable oil, or any combination thereof.

Examples of suitable pharmaceutically acceptable stabilizers may include may include, but not limited to aminoethyl sulfonic acid, L-arginine, butylhydroxyanisol, polyvinylpyrrolidone, L-cysteine, cysteine hydrochloride, diethanolamine, diethylenetriaminepentaacetic acid, ferric chloride, inositol, D,L-methionine, or any combination thereof.

Examples of suitable pharmaceutically acceptable preservatives may include, but not limited to, chlorobutanol, benzalkonium chloride, methyl paraben, propyl paraben, benzoic acid, sodium benzoate, sorbic acid, benzethonium chloride, cetyl pyridinium chloride, benzyl bromide, benzyl alcohol, phenylmercury nitrate, phenylmercury acetate, thiomersal, merthiolate, chlorhexidine, phenylethyl alcohol, quaternary ammonium chloride, sodium benzoate, sodium propionate, or any combination thereof.

Examples of suitable pharmaceutically acceptable antioxidants may include, but not limited to, butylated hydroxytoluene (BHT), butylated hydroxyanisole (BHA), propyl gallate, monothioglycerol, ascorbic acid, sodium ascorbate, erythorbic acid, potassium metabisulfite, sodium metabisulfite, propionic acid, sodium formaldehyde sulphoxylate, reduced glutathione, thiourea, cysteine, n-acetylcysteine, methionine, sodium sulfite, sodium bisulfate, alkyl gallate, including propyl gallate, vitamin E, or other tocopherol analogs, including tocopherol acetate or TPGS, or any combination thereof.

The stable aqueous parenteral solution of the present invention may comprise monothioglycerol in a concentration of between about 1 mg/mL and about 10 mg/mL, for example, about 2 mg/mL, about 4 mg/mL, about 5 mg/mL, about 6 mg/mL or about 8 mg/mL.

Examples of suitable pharmaceutically acceptable surfactants may include, but not limited to, amphoteric, non-ionic, cationic or anionic molecules.

Suitable surfactants may include, but not limited to, polysorbates 80 (e.g. tween 80 etc.), poloxamer (poloxamer 188), sodium lauryl sulfate, lauryl dimethyl amine oxide, docusate sodium, cetyl trimethyl ammonium bromide (CTAB), polyvinyl alcohol, polyethoxylated alcohols, polyoxyethylene sorbitan, octoxynol, polyoxyl lauryl ether, Brij® surfactants (polyoxyethylene vegetable-based fatty ethers derived from lauryl, cetyl, stearyl and oleyl alcohols), bile salts (such as sodium deoxycholate and sodium cholate), polyoxyl castor oil, nonylphenol ethoxylate, lecithin, polyoxyethylene surfactants, phospholipids such as dimyristoylphosphatidyl glycerol (DMPG), disteroylphosphatidylethanolamine (DSPE), 1,2-Distearoyl-phosphatidylethanolamine-methyl-polyethyleneglycol conjugate (DSPE-mPEG), monoalkanolamine condensates, polyoxyethylene fatty acid amides, quaternary ammonium salts, polyoxyethylene alkyl and alicyclic amines, polyoxyethylene, sorbitan monolaurate and stearate, Solutol® (ethylene oxide/12-hydroxy stearic acid), tyloxapol, or any combination thereof.

The stable aqueous parenteral solution of the present invention may comprise polysorbate 80 in a concentration of between about 1 mg/mL and about 100 mg/mL, for example, about 2 mg/mL, about 5 mg/mL, about 7 mg/mL, about 10 mg/mL, about 20 mg/mL, about 40 mg/mL, about 50 mg/mL, about 60 mg/mL or about 80 mg/m L.

Examples of suitable pharmaceutically acceptable buffering agents may include, but not limited to, acetate (e.g. sodium acetate etc.), citrate (e.g. citric acid/sodium citrate etc.), phosphate (e.g. monobasic sodium phosphate, dibasic sodium phosphate etc.), carbonate, or any combination thereof.

Examples of suitable pharmaceutically acceptable nucleation inhibitors may include, but not limited to, polyvinylpyrrolidone, crospovidone, hydroxypropylmethyl cellulose (HPMC), poloxamers, polysorbate, phospholipids such as dimyristoylphosphatidyl glycerol (DMPG), disteroylphosphatidylethanolamine (DSPE), 1,2-Distearoyl-phosphatidylethanolamine-methyl-polyethyleneglycol conjugate (DSPE-mPEG), or any combination thereof. In one embodiment, polyvinylpyrrolidone may be PVP K12, PVP K17, PVP K25, PVP K30, PVPK40 or PVP K90.

Examples of suitable pharmaceutically acceptable pH adjusting agents may include, but not limited to, sodium hydroxide, hydrochloric acid, boric acid, citric acid, acetic acid, phosphoric acid, succinic acid, potassium hydroxide, ammonium hydroxide, magnesium oxide, calcium carbonate, magnesium carbonate, malic acid, potassium citrate, sodium phosphate, lactic acid, gluconic acid, tartaric acid, fumaric acid, diethanolamine, monoethanolamine, sodium carbonate, sodium bicarbonate, triethanolamine, or any combination thereof. The stable aqueous parenteral solution may comprise one or more pH adjusting agents in an amount to provide pH of the solution between about 8 and about 9, for example about 8.5.

Examples of suitable pharmaceutically acceptable isotonicity adjusting agents may include, but not limited to, sodium chloride, potassium chloride, calcium chloride, magnesium chloride, glucose, sucrose, dextrose, mannitol, glycerol, or any combination thereof.

The stable aqueous parenteral solution of the present invention may comprise sodium chloride in a concentration of between about 1 mg/mL and about 5 mg/mL, for example, about 2 mg/mL, about 3 mg/mL or about 4 mg/m L.

In another embodiment, the stable parenteral solution may comprise about 75 mg/mL of diclofenac, about 200 mg/mL of polyvinylpyrrolidone, about 20 mg/mL of polysorbate 80, about 5 mg/mL of monothioglycerol, one or more pH adjusting agents, for example, NaOH and/or HCl in a quantity sufficient to adjust pH of the solution about 8.5 and quantity sufficient water.

In another embodiment, the stable parenteral solution may comprise about 75 mg/mL of diclofenac, about 150 mg/mL of polyvinylpyrrolidone, about 20 mg/mL of polysorbate 80, about 5 mg/mL of monothioglycerol, one or more pH adjusting agents, for example, NaOH and/or HCl in a quantity sufficient to adjust pH of the solution about 8.5 and quantity sufficient water.

In another embodiment, the stable parenteral solution may comprise about 75 mg/mL of diclofenac, about 160 mg/mL of polyvinylpyrrolidone, about 20 mg/mL of polysorbate 80, about 5 mg/mL of monothioglycerol, one or more pH adjusting agents, for example, NaOH and/or HCl in a quantity sufficient to adjust pH of the solution about 8.5 and quantity sufficient water.

In another embodiment, the stable parenteral solution may comprise about 25 mg/mL of diclofenac, about 70 mg/mL of polyvinylpyrrolidone, about 7 mg/mL of polysorbate 80, about 5 mg/mL of monothioglycerol, about 3 mg/mL of sodium chloride, one or more pH adjusting agents, for example, NaOH and/or HCl in a quantity to adjust pH of the solution about 8.5 and quantity sufficient water.

In another embodiment, the stable parenteral solution may comprise about 37.5 mg/mL of diclofenac, about 80 mg/mL of polyvinylpyrrolidone, about 10 mg/mL of polysorbate 80, about 5 mg/mL of monothioglycerol, about 2 mg/mL of sodium chloride, one or more pH adjusting agents, for example, NaOH and/or HCl in a quantity to adjust pH of the solution about 8.5 and quantity sufficient water.

In another embodiment, the present invention provides a stable parenteral solution comprising diclofenac, polyvinylpyrrolidone, polysorbate 80 and water, wherein the solution is substantially free of co-solvent(s), for example, dimethyl sulfoxide, N,N-dimethylformamide, N,N-dimethyl acetamide, benzyl alcohol, N-methyl pyrrolidone or glycerol formal, ethanol, transcutol, glycerol, cremophor (polyethoxylated castor oil), glycofurol, propylene glycol or polyethylene glycol. The term "substantially free of" as used herein, unless and otherwise specifically mentioned, means total amount of co-solvent(s) (organic and/or inorganic), if present in the solution, is less than 5% v/v of the solution, for example, less than 3% v/v, less than 1% v/v, or less than 0.5% v/v of the solution. The solution may be free of any co-solvent.

In another embodiment, the present invention provides a stable parenteral solution comprising diclofenac, polyvinlypyrrolidone and water, wherein diclofenac may be the only active ingredient present in the solution.

In another embodiment, the present invention provides a stable parenteral solution comprising diclofenac, polyvinlypyrrolidone and water, wherein the solution does not contain paracetamol (acetaminophen).

In another embodiment, the present invention provides a stable parenteral solution comprising diclofenac, polyvinlypyrrolidone and water, wherein the solution is not for any other route of administration except for the parenteral route of administration; for example, solution is not for the administration via ophthalmic route, otic route, topical route (application on skin) or oral route. The stable parenteral solution comprising diclofenac, polyvinlypyrrolidone and water is not an eye drop solution and/or ear drop solution.

In yet another embodiment, the present invention provides a method for the acute treatment of migraine attacks with or without aura in adults (18 years of age or older), the method comprising administering a solution comprising diclofenac via subcutaneous route.

In another embodiment, the present invention provides a stable parenteral solution comprising diclofenac, polyvinylpyrrolidone and water, wherein the solution is supplied/provided in a suitable packaging material, for example, in a glass vial, in a glass ampoule, in a pre-filled syringe, in a glass bottle, in a plastic bottle, in a plastic bag, etc. The pre-filled syringe contains various constituent parts, for example, a sterile clear USP Type-I siliconized glass syringe barrel (1 mL, cut flange with a gauge (29 size), hypodermic needle (½ inch) fitted with rigid needle shield and laminated bromobutyl plunger stopper for the barrel.

In another embodiment, the present invention provides a kit comprising an autoinjector which contains a pre-filled syringe (a pre-filled syringe assembled/placed in the autoinjector), wherein the pre-filled syringe contains a solution comprising diclofenac, polyvinylpyrrolidone and water.

In another embodiment, the present invention provides a kit comprising (a) a pre-filled syringe containing a solution comprising diclofenac, polyvinylpyrrolidone and water, and (b) an autoinjector device. The kit is suitable to administer the solution via subcutaneous route.

The autoinjector may be integrated with a needle stick protection feature and holds a pre-filled syringe containing a single dose, whereby the entire deliverable volume is expelled.

In another embodiment, the present invention provides a single-dose pre-filled syringe with an auto-injector, wherein the pre-filled syringe contains solution comprising 37.5 mg/mL diclofenac, polyvinylpyrrolidone and water, wherein the pre-filled syringe with an auto-injector is suitable to administer the effective amount of diclofenac dose via subcutaneous route for the acute treatment of migraine attacks with or without aura in adults 18 years of age or older.

In another embodiment, the present invention provides treatment of migraine attacks with or without aura in adults 18 years of age or older comprising administering to a human being in need thereof, diclofenac via subcutaneous route, wherein the onset of the action obtained after administering diclofenac via subcutaneous route is faster in comparison to the onset of action obtained after administering diclofenac via oral route, thereby providing quicker/faster onset of action.

In another embodiment, the present invention provides treatment of migraine attacks with or without aura in adults 18 years of age or older comprising administering to a human being in need thereof, diclofenac via subcutaneous route, wherein safety profile obtained after administering diclofenac via subcutaneous route may be better/improved in comparison to the safety profile obtained after administering diclofenac via oral route. The safety profile relates to, but not limited to, safety profile involving gastrointestinal (GI) adverse effects, for example, risk of GI ulceration, bleeding, and/or perforation.

In another embodiment, the present invention provides a diclofenac sodium injection, 37.5 mg/mL, in a single-dose pre-filled syringe with an auto-injector.

In another embodiment, the present invention provides a diclofenac sodium injection in a single-dose pre-filled syringe with an auto-injector, wherein the diclofenac is present in a therapeutically effective dose amount of 12.5 mg, 25 mg, 37.5 mg, 50 mg, 75 mg or 100 mg.

The stable aqueous parenteral solution does not contain any toxic and/or irritant ingredient, for example, any cyclodextrin derivative (HPBCD (hydroxypropyl-β-cyclodextrin), HPACD (hydroxypropyl-α-cyclodextrin), HPGCD (hydroxypropyl-γ-cyclodextrin), SBECD (sulfobutylether-β-cyclodextrin) etc.), transcutol, cremophor (polyethoxylated castor oil), glycofurol, propylene glycol and/or polyethylene glycol.

In another embodiment, the stable aqueous parenteral solution does not contain any local anesthetic, for example, lidocaine, prilocaine, tetracaine, bupivacaine, mepivacaine and/or xylocaine.

In another embodiment, the present invention provides a process for preparing a stable parenteral solution comprising diclofenac, polyvinylpyrrolidone, polysorbate 80, monothioglycerol and water. The process includes steps: (a) adding polyvinylpyrrolidone, polysorbate 80 and monothioglycerol into water to form a clear solution, (b) adding diclofenac into the solution prepared in step (a), and (c) adding pH adjusting agent, like NaOH/HCl to have a pH of the solution between about 8 and about 9. Additionally, the process may include adding an appropriate amount of NaCl at the step (a). The prepared solution may be subjected to a terminal sterilization process.

In another embodiment, the present invention provides a method for the treatment of pain and/or inflammation, the method comprising administering stable parenteral solution via parenteral route to a human being in need thereof. The parenteral route for the treatment of pain and/or inflammation is intravenous and/or intramuscular. The parenteral dose of diclofenac may range from about 12.5 mg to about 100 mg, for example, 15 mg, 20 mg, 25 mg, 30 mg, 35 mg, 37.5 mg, 40 mg, 45 mg, 50 mg, 55 mg, 60 mg, 65 mg, 70 mg, 75 mg, 80 mg, 85 mg, 90 mg or 95 mg. The pain may be migraine pain.

In another embodiment, wherein the pain is associated from acute and/or chronic pain, nociceptive pain-somatic and/or visceral, neuropathic pain-peripheral neuropathy, neuralgia, spinal cord compression, plexopathy, nociplastic pain-idiopathic pain, centralized pain, central hypersensitivity, mixed pain or any other kind of pain.

In another embodiment, the present invention provides a method for the treatment of migraine attacks with or without aura to a human being in need thereof, the method comprising administering solution comprising diclofenac via subcutaneous route. The solution may further comprise polyvinylpyrrolidone and water. The solution may contain therapeutically effective amount of diclofenac to treat the migraine attacks. The individual in need of treatment of migraine attacks is an adult (18 years of age or older). The treatment of migraine attacks is acute and/or chronic. The treatment of migraine attacks with or without aura to a human being in need thereof comprising administering the solution of the present invention when administered via subcutaneous route may provide faster onset of the action in comparison to the onset of action obtained after administering diclofenac via oral route.

In another embodiment, the present invention provides an improved pharmacokinetic profile in comparison to the oral composition of diclofenac CAMBIA®.

In another embodiment, the present invention provides an open label, randomized, four period, four-treatment, four-sequence, crossover, balanced, single dose comparative bioavailability study of diclofenac composition in human subjects.

In another embodiment, the present invention provides the pharmacokinetic parameters of diclofenac formulation administered subcutaneously to human subjects.

In another embodiment the pharmacokinetic parameters are measured after collection of blood samples at pre-dose (0.0 hour) and at 0.05, 0.083, 0.167, 0.25, 0.333, 0.5, 0.667, 0.833, 1.0, 1.333, 1.667, 2.0, 2.5, 3.0, 4.0, 6.0, 8.0, 10.0 and 12.0 hours post dose.

In another embodiment, the oral administration of diclofenac CAMBIA® provides a pharmacokinetic profile that may further be characterized by a mean $AUC_{0-last}$ of at least 2000 ng*ml/h, more preferably of at least 1000 ng*ml/h, the mean $T_{max}$ ranging from about 0.2 hrs to about 0.4 hrs and $C_{max}$ not less than 1000 ng/ml.

In another embodiment, the oral administration of diclofenac CAMBIA® provides a pharmacokinetic profile that may further be characterized by a mean $AUC_{0-last}$ of at least 2000 ng*ml/h, more preferably of at least 1000 ng*ml/h, the mean $T_{max}$ ranging from about 0.2 hrs to about 0.4 hrs and $C_{max}$ not less than 1000 ng/ml under fasting conditions.

The solution comprising therapeutically effective amount of diclofenac to treat the migraine attacks of the invention may provide concentration of drug in plasma of at least 300 ng/mL, for example, at least 400 ng/mL, at least 500 ng/mL, at least 600 ng/mL, at least 700 ng/mL, at least 800 ng/mL, at least 900 ng/mL, at least 1000 ng/mL, at least 1500 ng/mL, at least 2000 ng/mL, at least 2500 ng/mL, at least 3000 ng/mL, at least 3500 ng/mL, at least 4000 ng/mL, at least 4500 ng/mL, at least 5000 ng/mL, at least 5500 ng/mL, at least 6000 ng/mL, at least 7000 ng/mL, at least 7500 ng/mL, at least 8000 ng/mL, at least 8500 ng/mL, at least 9000 ng/mL, at least 9500 ng/mL or at least 10,000 ng/mL, in less than 15 minutes, when the solution is administered via subcutaneous route.

The solution comprising therapeutically effective amount of diclofenac to treat the migraine attacks of the invention may provide value of $T_{max}$ less than 60 minutes, for example, less than 50 minutes, less than 40 minutes, less than 30 minutes, less than 20 minutes, less than 15 minutes or less than 10 minutes, less than 9 minutes, less than 8 minutes, less than 7 minutes, less than 6 minutes, less than 5 minutes, less than 4 minutes, less than 3 minutes, less than 2 minutes or less than 1 minute, when the solution is administered via subcutaneous route to a human.

The solution comprising diclofenac to treat the migraine attacks of the invention may provide value of $C_{max}$ more than 1000 ng/mL, for example, more than 1100 ng/mL, more than 1200 ng/mL, more than 1300 ng/mL, more than 1400 ng/mL, more than 1500 ng/mL, more than 1600 ng/mL, more than 1700 ng/mL, more than 1800 ng/mL, more than 1900 ng/mL, more than 2000 ng/mL, more than 2100 ng/mL, more than 2200 ng/mL, more than 2300 ng/mL, more than 2400 ng/mL, more than 2500 ng/mL, more than 2600 ng/mL, more than 2700 ng/mL, more than 2800 ng/mL, more than 2900 ng/mL, more than 3000 ng/mL, more than 3500 ng/mL, more than 4000 ng/mL, more than 4500 ng/mL, more than 5000 ng/mL, more than 5500 ng/mL, more than 6000 ng/mL, more than 6500 ng/mL, more than 7000 ng/mL, more than 7500 ng/mL, more than 8000 ng/mL, more than 8500 ng/mL, more than 9000 ng/mL, more than 9500 ng/mL, more than 10,000 ng/mL, more than 10,500 ng/mL, more than 11,000 ng/mL, more than 11,500 ng/mL, more than 12,000 ng/mL, more than 12,500 ng/mL, more than 13,000 ng/mL, more than 13,500 ng/mL, more than 14,000 ng/mL, more than 14,500 ng/mL or more than 15,000 ng/mL, when the solution is administered via subcutaneous route to a human at a diclofenac dose of 12.5 mg, 25 mg, 37.5 mg, 50 mg, 75 mg or 100 mg.

The solution comprising diclofenac to treat the migraine attacks of the invention may provide value of $AUC_{last}$ more than 500 ng*h/mL, more than 600 ng*h/mL, more than 700 ng*h/mL, more than 800 ng*h/mL, more than 900 ng*h/mL, more than 1000 ng*h/mL, more than 1100 ng*h/mL, more than 1200 ng*h/mL, more than 1300 ng*h/mL, more than 1400 ng*h/mL, more than 1500 ng*h/mL, more than 1600 ng*h/mL, more than 1700 ng*h/mL, more than 1800 ng*h/mL, more than 1900 ng*h/mL, more than 2000 ng*h/mL, more than 2100 ng*h/mL, more than 2200 ng*h/mL, more than 2300 ng*h/mL, more than 2400 ng*h/mL, more than 2500 ng*h/mL, more than 2600 ng*h/mL, more than 2700 ng*h/mL, more than 2800 ng*h/mL, more than 2900 ng*h/mL, more than 3000 ng*h/mL, more than 3500 ng*h/mL, more than 4000 ng*h/mL, more than 4500 ng*h/mL, more than 5000 ng*h/mL, more than 5500 ng*h/mL, more than 6000 ng*h/mL, more than 6500 ng*h/mL, more than 7000 ng*h/mL, more than 7500 ng*h/mL, more than 10,000 ng*h/mL, more than 12,500 ng*h/mL, more than 15,000 ng*h/mL, more than 17,500 ng*h/mL, more than 20,000 ng*h/mL, more than 22,500 ng*h/mL or more than 25,000 ng*h/mL, when the solution is administered via subcutaneous route to a human at a diclofenac dose of 12.5 mg, 25 mg, 37.5 mg, 50 mg, 75 mg or 100 mg.

In another embodiment, the physical and chemical stability of the parenteral solution of the present invention was studied at 25° C. temperature and 60% relative humidity (% RH) as well as at 40° C. temperature and 75% RH.

Abbreviations

ND: Not Detected.
NMT: Not More Than.
BQL: Below Quantitation Limit.
BDL: Below Detection Limit.
NLT: Not Less Than.
q.s.: Quantity Sufficient.

The present invention is illustrated by the following examples which are provided to be exemplary of the invention and do not limit the scope of the invention.

Example 1

TABLE 1

| Sr. no. | Ingredients | Amount in mg |
|---|---|---|
| 1 | Diclofenac sodium | 1500 |
| 2 | Polyvinylpyrrolidone K12 | 4000 |
| 3 | Polysorbate 80 | 400 |
| 4 | Sodium hydroxide | q.s. to pH 8.5 |
| 5 | Monothioglycerol | 100 |
| 6 | Water for Injection | q.s. to 20 mL |

Process:

All the ingredients were used in an amount mentioned in Table 1, for preparing diclofenac injection solution, batch size 20 mL.

Polyvinylpyrrolidone K12, polysorbate 80 and monothioglycerol were added into 16 mL of water for injection, stirred and dissolved completely at controlled room temperature. Diclofenac sodium was added to the above prepared solution with moderate stirring at controlled room temperature. Then pH of the solution was adjusted to 8.5 using 5% w/v NaOH and/or 5% w/v HCl and the volume was made up to 20 mL using water for injection. The solution was filtered through a 0.22µ filter and filled into an amber colored glass vial.

Example 2

TABLE 2

| Solution | Amount in mg | |
|---|---|---|
| | Solution 2A | Solution 2B |
| Diclofenac sodium | 1500 | 1500 |
| Polyvinylpyrrolidone K12 | 3000 | — |
| Polysorbate 80 | 400 | 400 |
| Sodium hydroxide | q.s. to pH 8.5 | q.s. to pH 8.5 |
| Monothioglycerol | 100 | 100 |
| Water for Injection | q.s. to 20 mL | q.s. to 20 mL |

Process:

The process for preparing example 2 is the same as the process for preparing example 1, with the exception that solution 2A contains 150 mg/mL polyvinylpyrrolidone K12 and solution 2B does not contain polyvinylpyrrolidone K12.

The solution 2A and solution 2B were tested for their physical stability and chemical stability, and the results are reported in the Table 2A below.

TABLE 2A

| | Physical stability | | | Chemical stability (Impurity A) | |
|---|---|---|---|---|---|
| Storage conditions | Initial | 1 day/ 25° C. | 1 day/ 2-8° C. | Initial | 1 day/ 80° C. |
| Solution 2A | Clear solution | Clear solution | Clear solution | ND | 0.13% |
| Solution 2B | Unstable. Crystallization of diclofenac occurs within 2 minutes of preparing the solution. | — | — | ND | 0.35% |

It is evident from a comparison of the stability data for solution 2A and solution 2B, provided at the above Table 2A, that polyvinylpyrrolidone provides physical as well as chemical stability to diclofenac sodium in the liquid injection solution.

Example 3

TABLE 3

| Sr. no. | Ingredients | mg/mL |
|---|---|---|
| 1 | Diclofenac sodium | 75 |
| 2 | Polyvinylpyrrolidone K12 | 160 |
| 3 | Polysorbate 80 | 20 |
| 4 | Sodium hydroxide | q.s. to pH 8.5 |
| 5 | Hydrochloric acid | q.s. to pH 8.5 |
| 6 | Monothioglycerol | 5 |
| 7 | Water for Injection | q.s. to 1 mL |

Process:

All the ingredients were used in a concentration as mentioned in Table 3, for preparing diclofenac injection solution having a batch size 500 mL. In measured quantity of water for injection, nitrogen was sparged until dissolved oxygen was at a level upto 2 ppm. Polyvinylpyrrolidone K12 was added into 350 mL (70% amount of total batch size) of nitrogen sparged water for injection and dissolved by stirring at room temperature. Monothioglycerol was added into the above prepared solution. Polysorbate 80 was added to the above prepared solution and dissolved by stirring.

Diclofenac sodium was added to the above prepared solution and dissolved by stirring at room temperature. Then, pH of the solution was adjusted to 8.5 using 5% w/v NaOH and/or 5% w/v HCl, and the volume was made up to 500 mL using nitrogen sparged water for injection. The solution was filtered through a 0.2µ sterile filter and filled into a clear glass ampoule under pre- and post-nitrogen flushing.

The solution of Example 3 was tested for certain parameters at various storage conditions, viz., storage at 25° C. temperature and 60% RH as well as at 40° C. temperature and 75% RH and for various storage times, viz., 3 months (3M), 6 months (6M), 12 months (12M) and 24 months (24M). The results are reported in the Table 3A below.

TABLE 3A

| Storage conditions | Parameters | Initial | 3M | 6M | 12M | 24M |
|---|---|---|---|---|---|---|
| 25° C./ 60% RH | Description | Clear solution | Clear solution | Clear solution | Clear solution | Clear solution |
| | Assay (%) | 101.900 | 102.300 | 102.700 | 101.700 | 101.900 |
| | Impurity A | ND | ND | BQL | BQL | BQL |
| | pH | 8.720 | 8.450 | 8.480 | 8.360 | 8.590 |
| | Absorbance | 0.057 | 0.140 | 0.180 | 0.271 | 0.231 |
| | % Transmittance | 100.000% | 99.900% | 99.700% | 99.000% | 99.300% |
| | Viscosity (cP) | 6.310 | — | 5.910 | — | — |
| | Osmolality (mOsm) | 485 | 445 | 438 | 434 | 434 |
| 40° C./ 75% RH | Description | Clear solution | Clear solution | Clear solution | — | — |
| | Assay (%) | 101.900 | 103.000 | 102.700 | — | — |
| | Impurity A | ND | 0.02% | 0.11% | — | — |
| | pH | 8.720 | 8.370 | 8.450 | — | — |
| | Absorbance | 0.057 | 0.417 | 0.502 | — | — |
| | % Transmittance | 100.000% | 98.100% | 99.700% | — | — |
| | Viscosity (cP) | 6.310 | — | 5.930 | — | — |
| | Osmolality (mOsm) | 485 | 450 | 446 | — | — |

Measurement of absorbance and transmittance was done by UV spectrophotometer.

Measurement of viscosity was done by brookfield viscometer, model DV2T.

Measurement of osmolality (mOsm) was done by osmometer.

Measurement of assay (%) was done by HPLC (high performance liquid chromatography).

The solution of Example 3 was diluted using appropriate quantities of saline solution (0.9% sodium chloride) to achieve diluted solutions comprising diclofenac in a concentration of 0.75 mg/mL, 0.30 mg/mL, and 0.15 mg/mL. All three diluted solutions were tested for certain parameters (i) at initial time point ($T_0$), (ii) after 24 hours storage at controlled room temperature (25° C.±2° C.), and (iii) after 24 hours storage at 2-8° C. temperature. The results are reported in the Table 3B below.

TABLE 3B

| Diclofenac Na conc. (mg/mL) | Temp. | Description | pH $T_0$ | pH 24 hrs | Assay (%) $T_0$ | Assay (%) 24 hrs | Total Impurities $T_0$ | Total Impurities 24 hrs |
|---|---|---|---|---|---|---|---|---|
| 0.75 | CRT | Clear | 7.20 | 6.65 | 100.40 | 100.60 | BQL | BQL |
| 0.30 | CRT | Clear | 6.95 | 6.45 | 96.90 | 100.10 | 0.06 | 0.02 |
| 0.15 | CRT | Clear | 6.63 | 6.25 | 99.00 | 98.80 | ND | BQL |
| 0.75 | 2-8° C. | Clear | 7.20 | 6.50 | 100.50 | 101.10 | ND | BQL |
| 0.30 | 2-8° C. | Clear | 6.95 | 6.28 | 96.60 | 98.60 | BQL | BQL |
| 0.15 | 2-8° C. | Clear | 6.63 | 6.08 | 98.90 | 98.80 | BQL | BQL |

Example 4

TABLE 4

| Sr. no. | Ingredients | mg/mL |
|---|---|---|
| 1 | Diclofenac sodium | 25 |
| 2 | Polyvinylpyrrolidone K12 | 70 |
| 3 | Polysorbate 80 | 7 |
| 4 | Sodium chloride | 3 |
| 5 | Sodium hydroxide | q.s. to pH 8.5 |
| 6 | Hydrochloric acid | q.s. to pH 8.5 |
| 7 | Monothioglycerol | 5 |
| 8 | Water for Injection | q.s. to 1 mL |

Process:

All the ingredients were used in a concentration as mentioned in Table 4, for preparing diclofenac injection solution having a batch size 1400 mL. The process for preparing Example 4 is same as the process for preparing Example 3, with the exception that Example 4 contains an additional step of addition of sodium chloride and dissolved by stirring, after addition of polysorbate 80 and before the addition of diclofenac sodium.

The solution of Example 4 was tested for certain parameters at various storage conditions, viz., storage at 25° C. temperature and 60% RH as well as at 40° C. temperature and 75% RH and for various storage times, viz., 3 months (3M), 6 months (6M), 12 months (12M) and 18 months (18M). The results are reported in the Table 4A below.

TABLE 4A

| Storage conditions | Parameters | Initial | 3M | 6M | 12M | 18M |
|---|---|---|---|---|---|---|
| 25° C./ 60% RH | Description | Clear solution | Clear solution | Clear solution | Clear solution | Clear solution |
| | Assay (%) | 102.900 | 103.100 | 102.400 | 99.900 | 102.700 |
| | Impurity A | ND | BQL | BQL | BQL | 0.03% |
| | pH | 8.770 | 8.420 | 8.560 | 8.490 | 8.590 |
| | Absorbance | 0.034 | 0.067 | 0.099 | 0.156 | 0.178 |
| | % Transmittance | 99.500% | 98.800% | 99.000% | 98.900% | 98.600% |
| | Viscosity (cp) | 1.79 | — | — | — | — |
| | Osmolality (mOsm) | 340 | 329 | 335 | 306 | 311 |
| 40° C./ 75% RH | Description | Clear solution | Clear solution | Clear solution | — | — |
| | Assay (%) | 102.900 | 101.800 | 100.700 | — | — |
| | Impurity A | ND | 0.060% | 0.280% | — | — |
| | pH | 8.770 | 8.460 | 8.580 | — | — |
| | Absorbance | 0.034 | 0.215 | 0.234 | — | — |
| | % Transmittance | 99.500% | 98.900% | 98.800% | — | — |
| | Viscosity (cP) | 1.790 | — | — | — | — |
| | Osmolality (mOsm) | 340 | 315 | 326 | — | — |

Example 5

TABLE 5

| Sr. no. | Ingredients | mg/mL |
|---|---|---|
| 1 | Diclofenac sodium | 37.5 |
| 2 | Polyvinylpyrrolidone K12 | 80 |
| 3 | Polysorbate 80 | 10 |
| 4 | Sodium chloride | 2 |
| 5 | Sodium hydroxide | q.s. to pH 8.5 |
| 6 | Hydrochloric acid | q.s. to pH 8.5 |
| 7 | Monothioglycerol | 5 |
| 8 | Water for Injection | q.s. to 1 mL |

Process:

All the ingredients were used in a concentration as mentioned in Table 5, for preparing diclofenac injection solution having a batch size 500 mL.

The process for preparing Example 5 is same as the process for preparing Example 4.

The solution of Example 5 was tested for certain parameters parameters at various storage conditions, viz., storage at 25° C. temperature and 60% RH as well as at 40° C. temperature and 75% RH and for various storage times, viz., 3 months (3M), 6 months (6M), 12 months (12M) and 18 months (18M). The results are reported in the Table 5A below.

TABLE 5A

| Storage conditions | Parameters | Initial | 3M | 6M | 12M | 18M |
|---|---|---|---|---|---|---|
| 25° C./ 60% RH | Description | Clear solution | Clear solution | Clear solution | Clear solution | Clear solution |
| | Assay (%) | 103.200 | 103.900 | 102.6% | 104.2% | 102.7% |
| | Impurity A | BQL | 0.010% | 0.020% | 0.030% | 0.020% |
| | pH | 8.290 | 8.120 | 8.150 | 8.280 | 8.310 |
| | Absorbance | 0.047 | 0.139 | 0.156 | 0.282 | 0.371 |
| | % Transmittance | 99.700% | 99.500% | 99.400% | 99.200% | 97.800% |
| | Viscosity (cP) | 2.080 | — | — | — | — |
| | Osmolality (mOsm) | 334 | 322 | 326 | 322 | 315 |
| 40° C./ 75% RH | Description | Clear solution | Clear solution | Clear solution | Clear solution | — |
| | Assay (%) | 103.200 | 101.500 | 103.100 | 101.000 | — |
| | Impurity A | BQL | 0.090% | 0.310% | 0.650% | — |
| | pH | 8.290 | 8.170 | 8.220 | 8.290 | — |
| | Absorbance | 0.047 | 0.333 | 0.380 | 0.502 | — |
| | % Transmittance | 99.700% | 99.700% | 98.700% | 98.000% | — |
| | Viscosity (cP) | 2.080 | — | — | — | — |
| | Osmolality (mOsm) | 334 | 324 | 335 | 326 | — |

Example 6: Preparation of Pre-Filled Syringe Assembled/Placed in the Autoinjector The diclofenac solution for Example 6 is prepared in the same way as prepared in Example 5, except, filling of the solution into a clear glass ampoule, the solution has been filled into a glass syringe followed by assembling/placing the pre-filled syringe in an auto-injector.

The solution of Example 6 was tested for certain parameters at various storage conditions, viz., storage at 25° C. temperature and 60% RH as well as at 40° C. temperature and 75% RH and for various storage times, viz., 3 months (3M) and 6 months (6M). The results are reported in the Table 6 below.

TABLE 6

| Storage conditions | Parameters | Initial | 3M | 6M |
|---|---|---|---|---|
| 25° C./ 60% RH | Description | Clear solution | Clear solution | Clear solution |
| | Assay (%) | 101.500% | 101.000% | 101.400% |
| | Impurity A | ND | BDL | BDL |
| | pH | 8.4 | 8.3 | 8.3 |
| | Absorbance | 0.030 | 0.110 | 0.110 |
| | % Transmittance | 99.400% | 99.000% | 100.000% |
| | Osmolality (mOsm) | 322 | 317 | 312 |
| 40° C./ 75% RH | Description | Clear solution | Clear solution | Clear solution |
| | Assay (%) | 101.500% | 100.700% | 101.000% |
| | Impurity A | ND | 0.140% | 0.350% |
| | pH | 8.4 | 8.3 | 8.3 |
| | Absorbance | 0.030 | 0.300 | 0.410 |
| | % Transmittance | 99.400% | 98.900% | 99.700% |
| | Osmolality (mOsm) | 322 | 316 | 315 |

It is evident from a comparison of the stability data for Example 3, Example 4, Example 5 and Example 6, provided in the above Table 3A & 3B, Table 4A, Table 5A and Table 6, respectively that diclofenac solution of the present invention remains physically and chemically stable initially as well as upon storage at various storage conditions and primary packagings.

Example 7: Pharmacokinetic Study in Rats

Test product prepared in Example 5 was used for the study.

| | |
|---|---|
| Animal model | Wistar rat |
| Route of administration | IV (group 1), IM (group 2), SC (group 3) |
| Fasting/Non-fasting | Non fasting, free access of feed and water ad libitum |
| Dose | 3.9 mg/kg (37.5 mg human equivalent dose considering 60 kg human weight) |

Pharmacokinetic Parameters:

| Parameter | IM | SC |
|---|---|---|
| $C_{max}$ (ng/mL) | 5985.1 ± 1300.9 | 6419.1 ± 1093.6 |
| $AUC_{last}$ (ng * h/mL) | 4780.6 ± 787.0 | 5083.0 ± 866.5 |
| $AUC_{int}$ (ng * h/mL) | 4876.3 ± 818.0 | 5190.0 ± 926.3 |
| $T_{max}$ (minutes) | 15 | 10 |
| $T_{1/2}$ (hours) | 1.9 ± 0.5 | 2.0 ± 0.5 |
| Bioavailability (%) | ~73 (Comparative to IV) | ~77.5 (Comparative to IV) |

Example 8: Pharmacokinetic Study in Humans

| | |
|---|---|
| Title | Single dose comparative bioavailability study of two test formulations of Diclofenac Sodium Injection 37.5 mg/mL and 'CAMBIA ®' (diclofenac potassium), for oral solution 50 mg in healthy adult human subjects under fasting conditions. |
| Study Design | An open label, randomized, four period, four-treatment, four-sequence, crossover, balanced, single dose comparative bioavailability study. |
| Investigational products | Test Product (T1): Diclofenac Sodium Injection at a dose of 37.5 mg (1 mL) administered through Subcutaneous route<br>Test Product (T1): Diclofenac Sodium Injection at a dose of 24.75 mg (0.66 mL) administered through Subcutaneous route<br>Test Product (T2): Diclofenac Sodium Injection at a dose of 37.5 mg (10 mL) administered through Intravenous route<br>Reference Product (R): 'CAMBIA ®' |
| Administration of Investigational products | Test Product (T1) (Dose: 37.5 mg): Single dose (1 mL$) of test product (T1) Diclofenac Sodium Injection 37.5 mg/mL was administered to the subjects through subcutaneous route in the front side of the middle thigh approximately over 10 second in lying down position.<br>$1.0 mL will deliver 37.5 mg of Diclofenac Sodium<br>Test Product (T1) (Dose: 24.75 mg): Single dose (0.66 mL** ) of test product (T1) Diclofenac Sodium Injection 37.5 mg/ml was administered to the subjects through subcutaneous route in the front side of the middle thigh approximately over 10 second in lying down position.<br>**0.66 mL will deliver 24.75 mg of Diclofenac Sodium<br>Note: Test Product (T1) was administered on right side followed by left side in subsequent applicable period.<br>Test Product (T2) (Dose: 37.5 mg): Single dose (10 mL*) of test product (T2) Diclofenac Sodium Injection 37.5 mg/mL was administered to the subjects through intravenous route in arm vein approximately over 15 seconds in lying down position.<br>*10.0 mL will deliver 37.5 mg of Diclofenac Sodium.<br>Note: 1.0 mL of 37.5 mg/mL was diluted upto 10 ml by sterile 0.9 % normal saline to get final diluted solution of 3.75 mg/mL.<br>Reference Product (R):<br>One packet of reference product was administered with total 240 ml of water in sitting position as per below procedure. Within 05 minutes prior to dosing, the contents of the packet were dissolved in a glass with approximately 60 mL of the 240 mL of water. In order to prevent any powder remaining in the packet, the study personnel rinsed the packet with approximate 5 ml of water (using a syringe or a pipette) from the 240 mL of water and the contents were emptied into the glass. Study personal ensured that all powder was dissolved before dosing. Then, the subject was instructed to drink the contents of the glass. Immediately following dosing, the glass was rinsed twice with the remainder of the 240 ml of water and study personal ensured that any residual powder is dissolved. Then, the subject was instructed to drink the contents of the glass immediately.<br>Plasma samples were taken and analyzed to provide the values of $C_{max}$, $T_{max}$ and AUC using validated method. Statistical analysis were performed on the pharmacokinetic parameters using Phoenix WinNonlin Software (Version 6.4 or higher). |
| Randomization schedule Crossover design | The order of receiving the investigational product for each subject was determined according to a randomization schedule. Subjects were randomized to one of the four sequences: either RT1(37.5)T2T1(24.75) or T1(37.5)T2T1(24.75)R or T2T1(24.75)R T1(37.5) or T1(24.75)RT1(37.5)T2. |
| Food Restrictions | Fasting for at least 10 hours prior to dosing until at least 04 hours post-dose in each period. |
| Blood collection time | In each period, total 20 venous blood samples (04 mL each, except pre-dose 08 mL) will be collected at pre-dose (0.0 hour) and at 0.05, 0.083, 0.167, 0.25, 0.333, 0.5, 0.667, 0.833, 1.0, 1.333, 1.667, 2.0, 2.5, 3.0, 4.0, 6.0, 8.0, 10.0 and 12.0 hours post dose in labeled K2EDTA vacutainers through an indwelling cannula placed in the forearm vein/dorsal aspect of hand of the subjects. |

Pharmacokinetic Parameters:

| Parameter | R (50 mg Oral solution) | T1 (37.5 mg SC injection) | T1 (24.75 mg SC injection) | T2 (37.5 mg IV Injection) |
|---|---|---|---|---|
| $C_{max}$ (ng/ml) | 2165.1 ± 1163.6 | 947.7 ± 253.4 | 644.9 ± 160.4 | 8073.6 ± 1663.1 |
| $AUC_{last}$ (ng * h/mL) | 1306.7 ± 305.9 | 1948.5 ± 200.8 | 1269.9 ± 122.7 | 2029.2 ± 258.5 |
| $AUC_{inf}$ (ng * h/mL) | 1338.3 ± 304.2 | 1976.8 ± 203.8 | 1294.8 ± 122.6 | 2062.7 ± 203.8 |
| $T_{max}$ (hours) | 0.238 | 0.571 | 0.667 | 0.055 |
| $T_{1/2}$ (hours) | 1.069 ± 0.22 | 1.298 ± 0.35 | 1.054 ± 0.13 | 1.207 ± 0.2 |

An open label, randomized, four period, four-treatment, four-sequence, crossover, balanced, single dose comparative bioavailability study of diclofenac composition was carried out to evaluate the pharmacokinetic parameters of diclofenac composition after collecting blood samples at pre-dose (0.0 hour) and at 0.05, 0.083, 0.167, 0.25, 0.333, 0.5, 0.667, 0.833, 1.0, 1.333, 1.667, 2.0, 2.5, 3.0, 4.0, 6.0, 8.0, 10.0 and 12.0 hours post dose and also to compare the pharmacokinetic properties of oral and subcutaneous formulations of diclofenac in humans. Considering the pharmacokinetics parameters in the above table, it is clear that $C_{max}$ of T2 (37.5 mg IV Injection) is 8073.6±1663.1 ng/mL at $T_{max}$ 0.05 hours as compared to $C_{max}$ of T1 (37.5 mg SC Injection) which is 947.7±253.4 ng/mL at $T_{max}$ 0.57 hours. The area under the curve $AUC_{last}$ for IV injection of strength 37.5 mg is 2029.2±258.5 ng*h/mL. It is also observed that the formulation when administred i.v or s.c almost resulted in the similar values in terms of $AUC_{inf}/AUC_{last}$. Hence it is likely that formulation whether administered via i.v or s.c route remains same in treatment of the reducing the pain.

Without wishing to be bound to a theory, the formulation described in the present invention is believed to be an improved formulation of diclofenac sodium or pharmaceutical acceptable salts thereof which is stable, economical, and commercially scalable.

The formulation described in the present invention discloses diclofenac sodium or pharmaceutical acceptable salts for oral or parenteral administration via subcutaneous route and intravenous route thereof which is stable, economical, commercially scalable and highly desirable.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

We claim:

1. A method for the treatment of pain, the method comprising administering to a mammal, in need thereof, a solution, via subcutaneous route, comprising diclofenac composition, wherein the diclofenac sodium is present in a therapeutically effective concentration of between about 37.5 mg/mL and about 75 mg/mL, having pharmacokinetic parameters—
    i. maximum diclofenac plasma concentration $C_{max}$ value not more than 9000 ng/ml,
    ii. time to reach the maximum concentration $T_{max}$ of 5 minutes and
    iii. area under the curve $AUC_{last}$ value not more than 3000 ng*h/mL,
        wherein the diclofenac composition comprises polyvinylpyrrolidone, one or more pH adjusting agents, and water.

2. The method of claim 1, wherein the pharmaceutical composition when administered as subcutaneous dose of 37.5 mg in comparison to 37.5 mg intra venous of administration had similar $AUC_{last}$ and $AUC_{inf}$.

3. The method of claim 1, wherein the pharmacokinetic parameters were measured after blood collection at pre-dose (0.0 hour) and at 0.05, 0.083, 0.167, 0.25, 0.333, 0.5, 0.667, 0.833, 1.0, 1.333, 1.667, 2.0, 2.5, 3.0, 4.0, 6.0, 8.0, 10.0 and 12.0 hours post dose in human subjects.

4. The method of claim 1, wherein the pharmaceutical composition of diclofenac when administered as subcutaneous dose of 37.5 mg produces a $T_{max}$ of 0.5 hours as compared to $T_{max}$ of 0.2 hours produced by 50 mg oral route of administration.

5. The method of claim 1, wherein the pharmaceutical composition of diclofenac when administered as subcutaneous dose of 37.5 mg produces a $T_{1/2}$ of 1.29 hours as compared to $T_{1/2}$ of 1.24 hours produced by 37.5 mg intravenous route of administration.

6. A method for the treatment of pain, the method comprising administering to a mammal, in need thereof, a solution, via intramuscular route, comprising diclofenac composition, wherein the diclofenac sodium is present in a therapeutically effective concentration of between about 37.5 mg/mL and about 75 mg/mL, having pharmacokinetic parameters—
    i. maximum diclofenac plasma concentration $C_{max}$ value not more than 7500 ng/ml,
    ii. time to reach the maximum concentration $T_{max}$ of 15 minutes and
    iii. area under the curve $AUC_{last}$ value not more than 6000 ng*h/mL,
        wherein the diclofenac composition comprises polyvinylpyrrolidone, one or more pH adjusting agents, and water.

7. A method for the treatment of pain according to claim 1, the method comprising administering to a mammal in need thereof, via parenteral route, therapeutically effective amount of diclofenac composition, wherein the pain is associated from acute and/or chronic pain, nociceptive pain-somatic and/or visceral, neuropathic pain-peripheral neuropathy, neuralgia, spinal cord compression, plexopathy, nociplastic pain-idiopathic pain, centralized pain, central hypersensitivity, mixed pain.

8. A method for the treatment of pain according to claim 6, the method comprising administering to a mammal in need thereof, via parenteral route, therapeutically effective amount of diclofenac composition, wherein the pain is associated from acute and/or chronic pain, nociceptive pain-somatic and/or visceral, neuropathic pain-peripheral neuropathy, neuralgia, spinal cord compression, plexopathy, nociplastic pain-idiopathic pain, centralized pain, central hypersensitivity, mixed pain.

9. A method according to claim 1, wherein the diclofenac composition is administered via an Autoinjector.

* * * * *